United States Patent

Jaffe et al.

[11] Patent Number: 5,856,508
[45] Date of Patent: Jan. 5, 1999

[54] FLUORESCENT YELLOW 1,2,3,4-TETRACHLORO-11H-ISOINDOLO-[2,1-A]-BENZIMIDAZOL-11-ONE PIGMENTS

[75] Inventors: Edward E. Jaffe, Wilmington, Del.; Martin Tanner, Tentlingen, Switzerland

[73] Assignee: Ciba Specialty Chemicals Corporation, Tarrytown, N.Y.

[21] Appl. No.: 153,550

[22] Filed: Nov. 16, 1993

Related U.S. Application Data

[63] Continuation of Ser. No. 924,208, Aug. 3, 1992, abandoned, which is a continuation-in-part of Ser. No. 737,799, Jul. 26, 1991, abandoned, which is a continuation of Ser. No. 520,487, May 8, 1990, abandoned.

[51] Int. Cl.$^6$ ................................................. C07D 239/70
[52] U.S. Cl. ........................................................ 548/301.7
[58] Field of Search ........................................... 548/301.7

[56] References Cited

U.S. PATENT DOCUMENTS

| | | | |
|---|---|---|---|
| 2,985,661 | 5/1961 | Hein et al. | 548/301.7 |
| 3,538,095 | 11/1970 | Christmann et al. | 548/301.7 |
| 3,904,791 | 9/1975 | Iverson | 427/277 |
| 3,922,232 | 11/1975 | Schein | 252/301.5 |
| 3,936,471 | 2/1976 | Sulkowski et al. | 548/301.1 |
| 3,939,093 | 2/1976 | Paperfuhs | 252/301.35 |
| 4,058,529 | 11/1977 | Graf et al. | 544/282 |
| 4,077,961 | 3/1978 | Gunter et al. | 546/41 |
| 4,154,618 | 5/1979 | Burke | 106/27 B |
| 4,623,379 | 11/1986 | Baum et al. | 548/301.7 |
| 4,963,600 | 10/1990 | Coughlin | 523/333 |

FOREIGN PATENT DOCUMENTS 59-185349  10/1984  Japan .

OTHER PUBLICATIONS

Chem. Abst. 102 (20) : 176456 S
Chem. Abst. 86: 56755
Chem. Abst. 74: 14191
Hine, Physical Organic Chemistry, pp. 85–87, 89 (1967).

*Primary Examiner*—Robert Gerstl
*Attorney, Agent, or Firm*—Kevin T. Mansfield; Jacob M. Levine

[57] ABSTRACT

Fluorescent yellow pigments comprising 1,2,3,4-tetrachloro-11H-isoindolo-[2,1-a]-benzimidazol-11-one and various derivatives thereof; the use of said pigments in a variety of substrates such as alkyds, enamels, inks and the like; a process for the preparation thereof involving the condensation of the appropriate o-phenylenediamine and tetrachlorophthalic anhydride; and the aforementioned novel derivatives of said compound.

10 Claims, No Drawings

FLUORESCENT YELLOW 1,2,3,4-TETRACHLORO-11H-ISOINDOLO-[2,1-A]-BENZIMIDAZOL-11-ONE PIGMENTS

This application is a continuation of application Ser. No. 07/924,208, filed Aug. 3, 1992, now abandoned, which is a continuation-in-part of Ser. No. 07/737,799, filed Jul. 26, 1991, now abandoned, which in turn is a continuation of Ser. No. 07/520,487, filed May 8, 1990, now abandoned.

The compound 1,2,3,4-tetrachloro-11H-isoindolo-[2,1-a]-benzimidazol-11-one was first described in the literature in 1921 by A. Bistrzycki and A. Lecco (Helv. Chim. Acta. 4, 425 [1921]) who synthesized the compound by melting an equa-molar mixture of tetrachlorophthalic acid and ortho-phenylenediamine in a bath heated at 250° C.

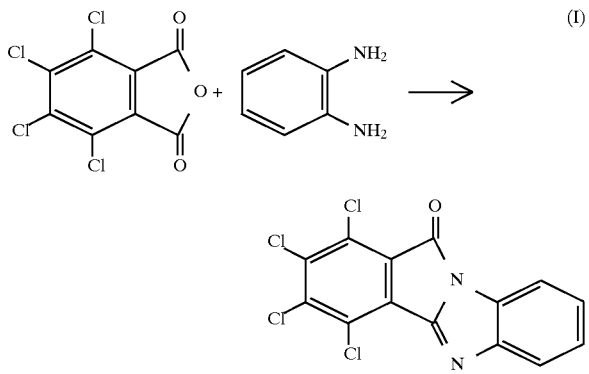

(I)

In the process, the tetrachlorophthalic acid was assumed to be converted to the tetrachlorophthalic anhydride which reacted with o-phenylenediamine to form a crude product which upon recrystallization from nitrobenzene gave a 60% yield of I. Subsequently, it was also shown that the two starting materials could be refluxed in nitrobenzene to produce the same product in 76% yield.

The same compound was also described in U.S. Pat. No. 2,985,661 where the synthesis was accomplished by heating the two starting materials in polyphosphoric acid at 250° C. The isolated product was extracted with 10% aqueous sodium carbonate followed by extraction of the dry residue with boiling nitrobenzene. The cooled extract was diluted with anhydrous diethyl ether to yield the yellow compound I, which was further purified by a recrystallization from xylene. The product was indicated to exhibit greenish-yellow fluorescence under ultraviolet irradiation. A general statement is made that it could function as a pigment for lacquers.

The same compound as well as the tetrabromo derivative thereof were disclosed in JP-A 59-185,349/1984 for use as an electrostatic image developing toner. Similar types of compounds containing acyloxy substituents were disclosed in DE-A 2,236,555 as dyes for hydrophobic fibrous materials. Corresponding naphthoyl derivatives were disclosed in Chemical Abstracts 66, 47303d (1967).

In pigment technology, it has long been recognized that lightfastness of any pigment is a function of crystallinity and particle size of the pigment. This is of particular importance in the instance where the compound absorbs light and is promoted to a higher state, probably a singlet state, where its residence is long enough to show visible emission of light or fluorescence. Reasonably long residence in an excited state is known to cause a variety of chemical reactions. Molecules in their electronically excited state are generally easier to reduce or oxidize than molecules in the ground state.

Correspondingly, the current state of the art is such that no pigment is presently available which shows the unusual combination of light emission and outdoor durability. Most commercial fluorescent yellow or other fluorescent pigments are solutions of dyes in polymers, and although they are effective emitters of light, their lightfastness is poor. Whenever a pigment shows fluorescence under UV light excitation, it has unacceptable lightfastness or outdoor durability and when a pigment has acceptable lightfastness, it shows no fluorescence. As a consequence, objects colored with paints containing available fluorescent pigments must be regularly and repeatedly repainted to preserve the desirable visual effect of these coatings.

It has now been surprisingly found that the pigments prepared by the novel processes described in this application fluoresce by UV light excitation and, unexpectedly, show outstanding outdoor durability for a light-emitting substance. The pigments are obtained by a process in which the synthesis is accomplished and the particle size grown to the desired extent in a single step to provide the combination of light emission, coupled with good outdoor durability. Such a product is particularly desirable. Correspondingly, the pigments exhibit greater resistance to reduction or oxidation in part due to the large particle size of the pigment generated during synthesis.

The fluorescent pigments of the present invention are thus based on chemical compounds which are prepared by the condensation of ortho-phenylenediamine or substituted o-phenylenediamines and tetrachlorophthalic anhydride in the presence of specific solvent systems. The one-step process of the current invention is characterized by ease of operation and preparation of product in high yield, high purity, and appropriate particle size. The solvents are readily redistilled for reuse.

The fluorescent pigments prepared according to the process of the invention correspond to the formula

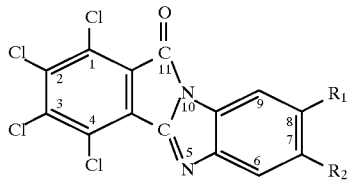

wherein $R_1$ and $R_2$ are independently hydrogen, halogen, $C_1$–$C_5$alkyl or $C_1$–$C_3$alkoxy.

Halogen is preferably chloro or fluoro; alkyl is preferably methyl and alkoxy is preferably methoxy.

Typical compounds include:
1,2,3,4,7-pentachloro-11H-isoindolo-[2,1-a]-benzimidazol-11-one,
1,2,3,4,8-pentachloro-11H-isoindolo-[2,1-a]-benzimidazol-11-one,
1,2,3,4-tetrachloro-7-fluoro-11H-isoindolo-[2,1-a]-benzimidazol-11-one,
1,2,3,4-tetrachloro-8-fluoro-11H-isoindolo-[2,1-a]-benzimidazol-11-one,
1,2,3,4,7-pentachloro-8-fluoro-11H-isoindolo-[2,1-a]-benzimidazol-11-one,
1,2,3,4,8-pentachloro-7-fluoro-11H-isoindolo-[2,1-a]-benzimidazol-11-one,
1,2,3,4-tetrachloro-7,8-dimethyl-11H-isoindolo-[2,1-a]-benzimidazol-11-one,
1,2,3,4-tetrachloro-8-methoxy-11H-isoindolo-[2,1-a]-benzimidazol-11-one, 1,2,3,4-tetrachloro-7-methoxy-11H-isoindolo-[2,1-a]-benzimidazol-11-one,
1,2,3,4-tetrachloro-7-methyl-11H-isoindolo-[2,1-a]-benzimidazol-11-one and
1,2,3,4-tetrachloro-8-methyl-11H-isoindolo-[2,1-a]-benzimidazol-11-one.

It is further to be noted that the invention additionally comprises novel compounds of the following formula

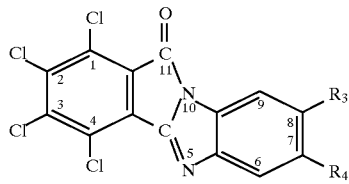

wherein $R_3$ and $R_4$ are independently hydrogen, halogen, $C_1$–$C_5$alkyl or $C_1$–$C_3$alkoxy, with the proviso that $R_3$ and $R_4$ are not both hydrogen.

The aforementioned preferences for $R_1$ and $R_2$ apply to these compounds. Particularly preferred are the pentachloro and tetrachloro-monofluoro compounds.

The pigments of this invention are prepared by reacting tetrachlorophthalic anhydride with o-phenylenediamine or the appropriately substituted o-phenylenediamine at elevated temperatures in the presence of a $C_2$–$C_5$alkanoic acid solvent, or hydrocarbon solvent or chlorinated hydrocarbon solvent and recovering said pigments. Typical substituted o-phenylenediamines include the 4-chloro, 4-fluoro, 4-fluoro-5-chloro, 4-methyl, 4,5-dimethyl and 4-methoxy derivatives. The preferred solvents are acetic acid or propionic acid without a catalyst, and xylene or dichlorobenzene with a catalyst with acetic acid being particularly preferred. The reaction generally proceeds at temperatures of from 100° to 160° C.

A preferred way of synthesis is running the reaction in the presence of an appropriate catalyst, particularly an arene sulfonic acid catalyst. Preferred catalysts are benzene sulfonic acid and alkyl, especially 4-alkyl, substituted benzene sulfonic acids. p-Toluene sulfonic acid is particularly preferred. The preferred amount of catalyst used is in the range of 1–5% by weight of the reactants.

For environmental reasons, xylene is preferred over the chlorinated 1,2dichlorobenzene. However, when reflexing in xylene as a solvent, the yield of the fluorescent pigment is only 59.2% (Example IV). When the appropriate acid catalyst is introduced, the yield goes up to 93% of theory (Example II).

The resulting compounds are fluorescent under UV light and, as a direct result of the synthetic process, will exhibit desirable large particle sizes generally ranging from 0.5 to 4.0 micrometers.

It will be understood that depending on the relative reactivities of the two amino groups in the substituted o-phenylenediamines a mixture of two isomeric products is usually obtained when unsymmetrically substituted o-phenylenediamines are used as starting materials. For example, when reacting tetrachlorophthalic anhydride with 4-methyl-o-phenylenediamine (3,4-diamino-toluene), a mixture of 1,2,3,4-tetrachloro-7-methyl- and 1,2,3,4-tetrachloro-8-methyl-11H-isoindolo-[2,1-a]-benzimidazol-11-one will be obtained.

The combination of light emission, excellent outdoor durability, and desirable intense yellow color qualifies the instant products as pigments for many applications, among them, automotive finishes, industrial finishes, road markings, printing inks, etc. The organic material colored with the instant pigments can vary in a wide range, such as from acrylics to alkyds to polyesters and polyurethanes.

Pigmented systems which contain the pigments as a component of mixtures of substances, possibly in addition to other components, include: pastes, flush pastes, preparations, printing colors, distempers, binder colors or lacquers and varnishes of all kinds, such as physically and oxidatively drying lacquers and varnishes, acid, amine and peroxide curing varnishes or polyurethane varnishes. The pigments may also be present in synthetic, semi-synthetic or natural macromolecular substances, such as thermoplastic resins, e.g., polyvinyl chloride, polystyrene, polyethylene, polyesters, phenoplasts, aminoplasts and rubber. The pigments may also be present in admixture with natural, regenerated or synthetic fibers, such as glass, silicate, asbestos, wood cellulose, acetylcellulose, polyacrylonitrile, polyester, polyurethane and polyvinyl chloride fibers or mixtures of the same, and also in powders, for example, other organic or inorganic pigments.

The mixtures of substances which contain as active coloring ingredient the pigments of this invention, may be of solid, elastic, pasty, viscous, mobile or thixotropic consistency. They may be obtained by conventional methods. Aqueous pastes may be obtained for example by stirring the pigments into water, possibly with the addition of a wetting or dispersing agent or by stirring or kneading the pigments into a dispersing agent in the presence of water and possibly of organic solvents or oils. These pastes may for example be used for the production of flush pastes, printing colors, distempers, plastic dispersions and spinning solutions. The pigments may also be introduced by stirring, rolling, kneading or grinding into water, organic solvents, non-drying oils, drying oils, lacquers, varnishes, plastics or rubber. Finally, it is also possible to work up the pigments by dry mixing with organic or inorganic masses, granulates, fibrous materials, powders and other pigments, to form mixtures of substances.

Since the instant pigments are fluorescent but transparent due to their relatively large particle size, they are best applied as a topcoat on a $TiO_2$— loaded basecoat in order to enhance visual appeal. Beyond that, one can optionally apply a third clearcoat. It is to be recognized, however, that UV absorbers in the clearcoat will tend to diminish or eliminate emission from the pigment simply because the exciting radiation of about 350 nm will be partially or completely screened out by the UV absorbers. Nevertheless, the absorption color of these pigments by themselves provides a pleasing yellow color. The pigments can also be used in combination with other yellows to enhance their intensity due to the fluorescence. In combination with other pigments, such as Indanthrone Blue, in a concentration ratio of, for example, 95% fluorescent pigment to 5% Blue, a green fluorescent pigment is obtained. Other combinations, as well as pigment ratios, are possible. For example, enhanced brightness is observed in the combination with a green-shade yellow isoindolinone pigment. Thus, in an acrylic basecoat containing 50/50 isoindolinone/$TiO_2$, and a topcoat of full-shade product of this invention, one obtains an attractive finish, even if a top clearcoat is applied.

Relative specifically to the use of the unsubstituted tetrachloro product, said pigment is utilized for purposes of this invention in alkyds, enamels and inks. Since lacquers, as referred to in U.S. Pat. No. 2,985,661, comprise resins prepared in their ultimate molecular weight to which the pigment is then added, the retention of performance characteristics by the pigment in enamels and alkyds which necessarily undergo crosslinking upon drying and wherein the pigment is present during such crosslinking is most meaningful.

The following examples further illustrate the embodiments of this invention. In these examples, all parts given are by weight unless otherwise indicated.

EXAMPLE I

The pigment of formula I above exhibiting desirable particle size and high yield is prepared in the following manner. A three liter round-bottom flask equipped with a stirrer, thermometer, reflux condenser, and nitrogen inlet is charged with 81 parts of o-phenylenediamine, 214.5 parts of tetrachlorophthalic anhydride, and 1,574 parts glacial acetic acid. Under a blanket of nitrogen, the mixture is stirred and heated to reflux in about 40 minutes. The heavy, white dispersion of the reaction mixture is difficult to stir but, upon heating, becomes progressively easier to stir and at about 60° C. the solid goes partially into solution and a yellow precipitate begins to form at about 90° C.

At reflux and as the particle size of the pigment grows to an average size of 0.5 to about 4 micrometers, stirring becomes easy. Reflux is continued for six hours. The initial reflux temperature of 115.5° C. eventually drops to 114.5° C. due to generation of two moles of water as a product of the reaction. The slurry is cooled to 75° C. and the solid isolated by filtration. The solid is washed with about 330 parts of methanol and then with water until the filtrate is acid free. Alternatively, the methanol can be omitted and the product washed directly with water. The yield is 243.2 parts, or 90.6% of the theoretical value. The dry pigment is pulverized and is ready for use. Direct analysis of the product shows 39.2% chlorine vs. calculated 39.68%.

A sample recrystallized from o-dichlorobenzene shows the following elemental analysis for formula $C_{14}H_4Cl_4N_2O$ with a molecular weight of 358.

| Calculated: | % C = 46.9 | Found: | % C = 46.9 |
|---|---|---|---|
| | % H = 1.12 | | % H = 1.10 |
| | % N = 7.82 | | % N = 7.62 |
| | % Cl = 39.7 | | % Cl = 39.3 |

EXAMPLE II

A mixture of 60 parts tetrachlorophthalic anhydride and 22.8 parts of o-phenylenediamine is suspended at room temperature in 389 parts xylene (mixture of isomers). After heating to 80° C., 1 part p-toluene sulfonic acid is added and heating is continued to reflux temperature. The reaction mixture is held at reflux temparature for 3 hours, while allowing water to distill off. After cooling to room temperature, the bright yellow solid is filtered, washed with methanol and water, and dried. The yield is 70 parts (93% of theory).

The product shows the following elemental analysis for formula $C_{14}H_4Cl_4N_2O$.

| Calculated: | % C = 46.9 | Found: | % C = 46.8 |
|---|---|---|---|
| | % H = 1.12 | | % H = 1.31 |
| | % N = 7.82 | | % N = 7.77 |
| | % Cl = 39.7 | | % Cl = 39.1 |

EXAMPLE III

Example II is repeated by using 4 parts of p-toluene sulfonic acid without distillation of water formed during the reaction, giving a yield of 90%.

EXAMPLE IV

A mixture of 14.3 parts tetrachlorophthalic anhydride and 5.4 parts o-phenylenediamine in 144 parts xylene is refluxed for five hours, while allowing water to distill off. The mixture is cooled to room temperature, and the solid isolated by filtration and washing with acetone free of xylene. The yield is 10.6 parts (59.2% of theory).

EXAMPLE V

A mixture of 28.6 parts tetrachlorophthalic anhydride and 10.8 parts o-phenylenediamine is reacted in 206 parts o-dichlorobenzene, under nitrogen at 180° C. for four hours, while allowing water to distill off. Upon cooling, filtration and washing with methanol, the yield is 28.2 parts, (79% of theory) of the yellow pigment.

EXAMPLE VI

A mixture of 15.2 parts tetrachlorophthalic anhydride and 5.7 parts o-phenylenediamine in 130 parts 1,2-dichlorobenzene is heated to reflux temperature. 1 part p-toluene sulfonic acid is added and the mixture is refluxed for 4 hours. After cooling to room temperature, the product is filtered and washed with 1,2-dichlorobenzene and ethanol and dried. The yield is 15.1 parts (81% of theory).

EXAMPLE VII

Example VI is repeated by using toluene instead of 1,2-dichlorobenzene, giving a yield of 85%.

EXAMPLE VIII

A mixture of 8.1 parts o-phenylenediamine, 21.5 parts tetrachlorophthalic anhydride, and 149 parts propionic acid are held with stirring under a blanket of nitrogen for 6 hours at 114°–115° C. The resulting product is filtered at 80°–85° C., washed with methanol and water, and dried. The yield of the yellow pigment is 24.5 parts (91.3% of theory). The elemental analysis is as follows:

| Calculated: | % C = 46.9 | Found: | % C = 47.1 |
|---|---|---|---|
| | % H = 1.13 | | % H = 0.80 |
| | % N = 7.82 | | % N = 7.34 |
| | % Cl = 39.71 | | % Cl = 39.6 |

Alternatively, the synthesis can be conducted at the boiling point of propionic acid with similar results.

A series of derivatives are prepared by the procedure of Example I, again using acetic acid as the solvent.

EXAMPLE IX

Using 4-chloro-o-phenylenediamine, the yield is 90.2%.

| Calculated: | % C = 42.8 | Found: | % C = 42.7 |
|---|---|---|---|
| | % H = 0.76 | | % H = 0.67 |
| | % N = 7.14 | | % N = 6.96 |
| | % Cl = 45.2 | | % Cl = 45.2 |

EXAMPLE X

Using 4-fluoro-o-phenylenediamine, the yield is 84.4%.

| Calculated: | % C = 44.7 | Found: | % C = 44.6 |
|---|---|---|---|
| | % H = 0.80 | | % H = 0.80 |
| | % N = 7.45 | | % N = 7.35 |
| | % Cl = 37.8 | | % Cl = 38.0 |

EXAMPLE XI

Using 4-fluoro5-chloro-o-phenylenediamine, the yield is 90.6%.

| Calculated: | % C = 40.9 | Found: | % C = 40.8 |
|---|---|---|---|
| | % H = 0.49 | | % H = 0.40 |
| | % N = 6.82 | | % N = 6.83 |
| | % Cl = 43.2 | | % Cl = 42.8 |

EXAMPLE XII

Using 4,5-dimethyl-o-phenylenediamine, the yield is 89.4%.

| Calculated: | % C = 49.7 | Found: | % C = 48.8 |
|---|---|---|---|
| | % H = 2.07 | | % H = 1.82 |
| | % N = 7.25 | | % N = 6.82 |
| | % Cl = 36.8 | | % Cl = 36.5 |

EXAMPLE XIII

Using 4-methoxy-o-phenylenediamine hydrochloride, the yield is 63.9%.

| Calculated: | % C = 46.4 | Found: | % C = 46.4 |
|---|---|---|---|
| | % H = 1.55 | | % H = 1.41 |
| | % N = 7.22 | | % N = 7.03 |
| | % Cl = 36.6 | | % Cl = 36.5 |

EXAMPLE XIV

A mixture of 2.44 parts of 3,4-diaminotoluene, 5.72 parts of tetrachlorophthalic anhydride, and 60 parts glacial acetic acid is refluxed with stirring for 6 hours. The resulting slurry is cooled to 100° C. and the product isolated by filtration. The solid is washed with methanol, followed by water until the filtrate is neutral to litmus. The dried pigment yield is 6.25 parts or 84.0% of theory.

The directly isolated product shows the following elemental analysis for formula $C_{15}H_6Cl_4N_2O$.

| Calculated: | % C = 48.4 | Found: | % C = 48.5 |
|---|---|---|---|
| | % H = 1.61 | | % H = 1.48 |
| | % N = 7.53 | | % N = 7.43 |
| | % Cl = 38.2 | | % Cl = 38.4 |

In summary, this invention is seen to provide a series of fluorescent pigments, improved methods for the synthesis thereof and compositions with unexpected performance characteristics stemming from the presence of said pigments therein. Variations may be made in procedures, proportions and materials without departing from the scope of the invention as defined in the following claims.

EXAMPLE XV

The intensities of maximum emission obtained by excitation with 365 nm light are denoted on a comparative emission scale.

| Compound of Example | Emission Value |
|---|---|
| I | 815 |
| V | 189 |
| VI | 79 |
| VII | 144 |
| VIII | 95 |

EXAMPLE XVI

A commercial alkyd resin dispersion [57 parts alkyd resin (60% solids), 34.2 parts melamine (50% solids), 1.9 parts xylene, and 1.9 parts methyl glycol (2-methoxyethanol)], 5 parts of pigment of Example I and 230 parts of 8 mm diameter ceramic balls in a 400 ml glass jar are dispersed for 72 hours by rotation at 120 RPM. The resulting dispersion is let down with xylene to 25 sec./#4 Ford Cup viscosity and sprayed as a masstone showing the typical yellow color with light emission upon excitation with a 350 nm UV lamp.

After 1,000 hours exposure in the Weather-o-meter, the performance reading (based on visual observation of color change of an exposed sample versus an unexposed sample with a scale of 5 reflecting no color change and 0 reflecting total color disappearance) is 4 out of the possible 5, whereas a commercial fluorescent yellow dye in polymer solution (RADGLO Yellow RS-10) shows a 1 or poor lightfastness.

EXAMPLE XVII

This example illustrates the incorporation of the pigment into a printing ink.

A mixture of 80% offset "Varnish 85" and 20% pigment of Example I is subjected to three passes on a Bühler triple roll mill. The temperature of the rolls is kept at 30° C., with the first and second passes being carried out with a line pressure of 1 MPa (10 bars) and the third pass at 2.3 MPa (23 bars) pressure.

The ink is drawn down on special paper (APCO II/II) and its lightfastness and light emission determined. The ink fluoresces under a UV (350 nm) lamp and shows lightfastness (color change between unexposed and exposed sample with 8 reflecting no color change and 0 reflecting total color disappearance) of 6–7 by exposure in a Fade-o-meter. By comparison, CI pigment yellow 101, a fluorescent pigment, shows a lightfastness reading of only 1.

One ink prepared in exactly the same manner but consisting of 95 parts pigment of Example I and 5 parts of Indanthrone Blue produces a green fluorescent ink with excellent lightfastness and a reading of 6–7.

EXAMPLE XVIII

This example illustrates the incorporation of the pigment into an automotive thermosetting acrylic enamel.

A commercial acrylic resin [80 parts (50% solids) and 64 parts xylene], 16 parts of pigment of Example I and 380 parts of 13 mm diameter ceramic balls in a 400 ml glass jar are dispersed for 48 hours by rotation at 100 RPM.

One hundred sixty parts of the resulting millbase are mixed with 69.3 parts of the same commercial acrylic resin solution and 90.7 parts of xylene. One hundred fifty parts of the reduced millbase is effectively blended with 23.1 parts of a 65% solids melamine solution and the resulting paint reduced with a solvent blend (90/10 ratio of xylene/2-ethylhexyl acetate) to a spray viscosity of 17 sec. on #4 Ford Cup.

The paint is sprayed to hiding on a panel previously painted with a white (TiO$_2$-containing) thermosetting paint. The resulting panel shows significant fluorescence under irradiation with a UV lamp and upon exposure in Florida for one year shows relatively little color or fluorescence change. In contrast, a commercial fluorescent pigment dye in polymer solution (Saturn Yellow, Day-Glo, T-17) exhibited substantially total color fade after the same period of exposure.

EXAMPLE XIX

This example shows incorporation of the pigment into a two-coat system, polyester base coat/clear coat system.

A commercial polyester resin [58.2 parts (76% solids)], 82.6 parts aromatic hydrocarbon (mineral spirits), 19.2 parts pigment of Example I, and 380 parts of 13 mm diameter ceramic balls in a 400 ml glass jar are dispersed for 64 hours by rotation at 100 RPM. Seventy-four parts of the resulting millbase is effectively blended with 25.8 parts of a solution containing 58.2% solids of resin, melamine, and catalyst (aromatic sulfonic acid) and 0.2 parts of a 38% catalyst solution. The masstone pigment is reduced to 24 sec. #2 Fisher Cup viscosity with xylene and the paint sprayed to hiding. The base coat is flashed for 3 minutes at room temperature and two coats of a clear coat commercial acrylic solution paint (containing 68.3% resin) applied after adjustment to spray viscosity. The paint is baked for 30 minutes at 121° C.

The resulting panel is exposed in Florida, along with a commercial fluorescent dye in polymer solution, for 12 and 18 months. Instrumental readings of spectroreflectance from color differences between exposed and unexposed parts of a panel are taken.

| | ΔE (CIE LAB color difference determined under illuminant D$_{65}$) | |
|---|---|---|
| | 12 Months | 18 Months |
| Pigment of Example I | 2.89 | 3.54 |
| Commercial Pigment (Saturn Yellow, Day-Glo, T-17) | 95.3 | 96.6 |

Once again, the pigment of the present invention shows very good outdoor durability in contrast to the commercial pigment.

In summary, this invention is seen to provide a series of fluorescent pigments, improved methods for the synthesis thereof and compositions with unexpected performance characteristics stemming from the presence of said pigments therein. Variations may be made in procedures, proportions and materials without departing from the scope of the invention as defined in the following claims.

What is claimed is:

1. A process for preparing compounds of the formula

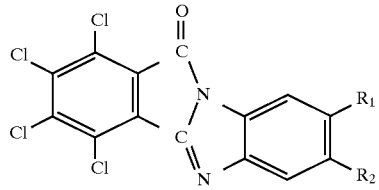

wherein $R_1$ and $R_2$ are independently hydrogen, halogen, $C_1$–$C_5$alkyl or $C_1$–$C_3$alkoxy, which comprises reacting tetrachlorophthalic anhydride with a compound of the formula

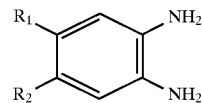

wherein $R_1$ and $R_2$ are defined as above, at elevated temperatures in the presence of an arene sulfonic acid catalyst and a solvent selected from the group consisting of dichlorobenzene, toluene and xylene and recovering said compound.

2. The process of claim 1, wherein the arene sulfonic acid catalyst is benzene sulfonic acid which is unsubstituted or substituted by $C_1$–$C_4$-alkyl.

3. The process of claim 1, wherein the arene sulfonic acid catalyst is p-toluene sulfonic acid.

4. The process of claim 1, wherein the amount of catalyst is in the range of 1–5% by wieght of the reactants.

5. The process of claim 1, wherein the solvent is xylene.

6. A process of claim 1 wherein the elevated temperatures are from 100° to 160° C.

7. A process of claim 1 wherein the compound is a pigment.

8. A process of claim 7 wherein said pigment is synthesized and grown in the same step.

9. A process of claim 8 wherein said pigment is selected from the group consisting of 1,2,3,4-tetrachloro-11H-isoindolo-(2,1-a)-benzimidazol-11-one, 1,2,3,4,7-pentachloro-11H-isoindolo-(2,1-a)-benzimidazol-11-one, 1,2,3,4,8-pentachloro-11H-isoindolo-(2,1-a)-benzimidazol-11-one, 1,2,3,4-tetrachloro-7-fluoro-11H-isoindolo-(2,1-a)-benzimidazol-11-one, 1,2,3,4-tetrachloro-8-fluoro-11H-isoindolo-(2,1-a)-benzimidazol-11-one, 1,2,3,4,7-pentachloro-8-fluoro-11H-isoindolo-(2,1-a)-benzimidazol-11-one, 1,2,3,4,8-pentachloro-7-fluoro-11H-isoindolo-(2,1-a)-benzimidazol-11-one, 1,2,3,4-tetrachloro-7,8-dimethyl-11H-isoindolo-(2,1-a)-benzimidazol-11-one, 1,2,3,4-tetrachloro-8-methoxy-11H-isoindolo-(2,1-a)-benzimidazol-11-one, 1,2,3,4-tetrachloro-7-methoxy-11H-isoindolo-(2,1-a)-benzimidazol-11-one, 1,2,3,4-tetrachloro-8-methyl-11H-isoindolo-(2,1-a)-benzimidazol-11-one, and 1,2,3,4-tetrachloro-7-methyl-11H-isoindolo-(2,1-a)-benzimidazol-11-one.

10. A process of claim 9 wherein said pigment is 1,2,3,4-tetrachloro-11H-isoindolo-(2,1-a)-benzimidazol-11-one.

* * * * *